(12) United States Patent
Bischoff

(10) Patent No.: US 6,531,859 B1
(45) Date of Patent: Mar. 11, 2003

(54) ELECTRONIC ARRANGEMENT FOR AN ELECTRIC COMPONENT AND AS A SUPPORT FOR SENSORS

(76) Inventor: Robert Bischoff, Carl-von-Ossietzky-Strasse 12, D-06114 Halle/Saale (DE)

( * ) Notice: Subject to any disclaimer, the term of this patent is extended or adjusted under 35 U.S.C. 154(b) by 0 days.

(21) Appl. No.: 09/831,987
(22) PCT Filed: Nov. 26, 1999
(86) PCT No.: PCT/DE99/03793
§ 371 (c)(1), (2), (4) Date: May 15, 2001
(87) PCT Pub. No.: WO00/34765
PCT Pub. Date: Jun. 15, 2000

(30) Foreign Application Priority Data

Dec. 10, 1998 (DE) .................... 298 22 007 U

(51) Int. Cl.⁷ .......................... G01N 27/00; G01N 7/00; G01F 1/68
(52) U.S. Cl. .................... 324/71.6; 324/71.1; 324/71.3; 324/71.5; 324/71.4; 73/31.05; 73/31.06; 73/204.26
(58) Field of Search .............. 324/71.6, 71.5, 324/71.1, 71.4, 71.3; 436/151; 422/53; 73/31.05, 31.06, 204.26

(56) References Cited

U.S. PATENT DOCUMENTS

| | | | | |
|---|---|---|---|---|
| 3,848,218 A | * | 11/1974 | Wakabayashi et al. ......... 338/35 |
| 4,358,951 A | | 11/1982 | Chang ........................ 73/31.05 |
| 4,387,165 A | | 6/1983 | Joungblood ................ 436/121 |
| 4,674,320 A | | 6/1987 | Hirschfeld ................. 73/31.06 |
| 4,761,710 A | * | 8/1988 | Chen .......................... 361/286 |
| 4,820,929 A | | 4/1989 | Modisette ............... 250/504 R |
| 4,885,929 A | * | 12/1989 | Kasahara et al. ............... 73/23 |
| 5,205,170 A | * | 4/1993 | Blechinger et al. ...... 73/204.26 |
| 5,277,068 A | * | 1/1994 | Fukiura et al. ................ 73/724 |
| 5,322,602 A | * | 6/1994 | Razaq .................... 204/153.22 |
| 5,348,761 A | * | 9/1994 | Mitter et al. ................. 427/101 |
| 5,387,462 A | | 2/1995 | Debe .......................... 428/323 |
| 5,483,164 A | * | 1/1996 | Moss et al. .................. 324/425 |
| 5,611,339 A | * | 3/1997 | Okabe et al. ............... 128/639 |
| 5,659,127 A | * | 8/1997 | Shie et al. .................. 73/31.05 |
| 5,731,584 A | * | 3/1998 | Beyne et al. ................ 250/374 |
| 5,783,154 A | * | 7/1998 | Althainz et al. .............. 422/98 |
| 5,945,700 A | * | 8/1999 | Mizutani .................... 257/259 |
| 5,985,673 A | * | 11/1999 | Bao et al. ................... 436/151 |
| 6,337,482 B1 | * | 4/2000 | Francke .................. 250/385.1 |
| 6,145,964 A | * | 11/2000 | Peter ........................... 347/55 |

FOREIGN PATENT DOCUMENTS

| | | |
|---|---|---|
| DE | 34 40 351 A | 6/1985 |
| EP | 0 755 695 A1 | 1/1997 |
| WO | 91 03734 | 3/1991 |

* cited by examiner

Primary Examiner—N. Le
Assistant Examiner—Wasseem H. Hamdan
(74) Attorney, Agent, or Firm—Michael J. Striker

(57) ABSTRACT

The invention relates to an electrode arrangement for an electronic component, also acting as a support for sensors. Said electrode arrangement is mounted on a substrate (1) as a suitably dimensioned surface-structure of two electro-conductive electrodes which are not electrically connected to one another. The electrode arrangement reproduces the conductivities and/or the substance of a sensor-active layer on the conductance of a measuring head or a functional element when said conductivities of the electrode arrangement and/or substance of a sensor-active layer are reproduced in a highly flexible manner. Said electrode arrangement can be produced in a simple and cost-effective manner. The invention provides for a plurality of conductive islands (3) which are not linked or not essentially linked to one another and which are mounted on a dielectric substrate (1) between two electrodes (2) in the form of a planar two-dimensional arrangement.

9 Claims, 1 Drawing Sheet

ELECTRONIC ARRANGEMENT FOR AN
ELECTRIC COMPONENT AND AS A
SUPPORT FOR SENSORS

BACKGROUND OF THE INVENTION

The invention describes an electrode arrangement for an electrical component and a carrier for sensors, which is applied on a carrier as a surface structure with suitable dimensions of two electrically conducting electrodes, which are not connected electrically with one another.

From the general state of technology, electrode arrangements are known for measuring probes of measuring devices for the examination of substances located between the electrodes, where the electrical characteristic values and their changes are evaluated. Examples of this are resistance measuring probes and measuring probes for electrolysis or electrophoresis.

It is also known that one can systematically use certain electrical characteristics with certain substances between the electrodes and an electrode structure with proper dimensions, whereby the complex resistance of such a surface structure acts as a transformer for voltage and current. Particular examples of this are the resistances and capacitors for thick and thin layer technology, whose adjustment to the final value is often achieved through the fine adjustment of the surface structure. This is done, for example, using systematic incisions with a laser. For this, the electrode material and the substance between them are suitably selected, In particular, air can be selected as a dielectric.

Using the special effects of substances and/or electrodes, electrical measuring devices can be produced using suitable surface structures for the examination of the measurement variables produced by the specific effect. Examples are, strain gauges, temperature sensitive elements, magnetic field measuring probes and luminous intensity measuring probes. Further examples, for the use of special effects based on particular adjustment of surface structures are function elements such as heating elements, which produce heat from the incoming supply of electrical energy or photocells, which recover electrical energy when illuminated.

For the formation of such surface structures, substances are employed, which are enriched with conductive filling materials. The filling materials are as a rule metal powder or soot and increase, essentially dependent on their volume share in the matrix, the total conductivity of the substance. This represents a microscopically three-dimensional heterogeneous system. This has the disadvantage that conductive three-dimensional conglomerates can be formed, which can easily lead to unforeseeable stochastically occurring one-dimensional current paths due to diffusion processes and a further disadvantage that these filling materials can also appear on the surface. Adhering agents can then come into direct contact with the filling materials and trigger undesired effects.

Through the proper design of the surface structure on the carrier, which structure is determined by the electrode form, the usable specific characteristic area of the electrodes and/or the substance can be represented with a suitable valuable of the measuring probe or of the function element. This applies particularly to the representation of the conductivity of the electrodes and/or of the substance in the conductance of the measuring probe of the function element. For higher conductivity, one attempts to produce current paths, which are as long and thin as possible, and for lower conductivity short and thick paths, whereby the electrodes with a large electrode edge surface with a lower electrode surface are formed to reinforce this effect. When producing the actual dimensions of suitable structures, one must continue to consider their influence on other characteristics, for example, on the inductance, possible line resonances or the maintenance of certain designated preferential directions.

In this way, resistances or capacities can be applied on a carrier as comb electrode structures, where the electrodes interlock like combs (interdigital resistor and interdigital capacitor), which allows a large electrode edge surface with a low electrode distance. The comb structures can be produced, for example, with technical photo means or imprinting followed by etching of the electrode substance or by cutting with a laser. The disadvantage with electrode structures produced with this procedure is the high technical expenditure required for the production and the resulting relatively high prices for the end product and in addition large surface structures can only be produced to a limited degree.

The European patent application, EP 0755695 A1, reveals an electrode with an applied paste or binding agent containing hydrophilic microgranulates of hydrophilic polymers or water soluble substances and electrically conductive microgranulates. The application of these electrodes is done particularly on living bodies for the measurement of leakage currents such as for an ECG or an EEG and in therapy for treatment with low frequency currents or the systematic application of active substances.

The electrode is to serve to transmit current from or to living bodies and thus to achieve therapeutic effects in addition to the measurements. Due to the material applied to the electrode, water is absorbed and irreversible changes in this layer are produced so that the electrode described as an electrical component or carrier for sensors, which is to be used for the determination of agents, is completely unsuitable.

The PCT application, WO 91/03734, describes the use and production of a resistance moisture sensor of plastic with the capability of swelling, which contains additives to increase the conductivity such as carbon, metal dust or similar things. The additives for increasing the conductivity are located in a three-dimensional polymer composition, whose position changes continually due to the swelling of the layer absorbing water, and the same applies to the geometry of the electrode, whereby disadvantageous effects occur for long-term applications. Strong swelling or quick changes in moisture conditions results in cracks in the polymer layer, which cannot be repaired.

The use as an electrical component or carrier for sensors for the detection of agents is not possible.

The purpose of the invention is to create an electrode arrangement for an electrical component and a carrier for sensors, which arrangement is applied on a substrate as a surface structure of suitable dimensions of two electrically conducting electrodes not electrically connected with one another; and which has a high flexibility for representation of the conductivities of the electrode arrangement and/or of the substance of a sensor-active layer, and which arrangement represents these through the conductance of a measuring probe or a function element and is simple and economical to manufacture.

SUMMARY OF INVENTION

The essence of the invention is that a number of conductive islands (passive electrodes) are applied on any given dielectric substrate, as a two-dimensional area arrangement, between two connection electrodes and these islands are not or are not essentially connected with one another and whereby relative to the complete filling of the interspace of the connection electrodes with the substance of the passive electrodes the conductance of the measuring probe or of the function element is changed. The total conductance of the measuring probe is dependent on the specific portion of the area of the passive electrodes. Because the two-dimensional distribution of the substance of the passive electrodes is only one dimension above that of a possible one-dimensional current path, the possibility of such a formation is very low. The remaining area of the substance represents a multiple non-contiguous area, in which the current paths spread in the area between the islands and around the islands. If when using a thin carrier, for example a foil, this is included in the flux, the islands influence the area of the carrier near to the surface structure and thus also the resulting total conductance. The advantages of such an electrode structure are found in particular in the high flexibility of the representation of the conductivities of the electrodes and/or of the substance by the conductance of a measuring probe or of a function element.

Such an island structure is, according to the invention, produced by the fine distribution of conductive substances on any insulation substrates, such as foils. The substance is firmly set on the substrate and can be sputtered on, steamed on, squirted on, dabbed on, imprinted or sprayed on, whereby a uniform distribution of the conductive islands exists.

As an option for the area island structure between the connection electrodes, these can also be arranged within special geometrical figures.

Variations of the carrier for sensors are coated on the surface with a material-selective substance, which determines the total conductance and are used as a detector for certain agents.

As an option, the substrate itself, if it is designed sufficiently thin, can also be coated so that the total conductance is essentially determined by the area close to the surface structure. The advantages of this design are found in the great variety concerning the type, form and size of the carrier and the economical manufacturing costs.

An additional advantageous form of the island structure can be created by the inclusion of hyperstructures with anisometries of substances with respect to the substrate, which the islands show in their short-range order, whereby an additional usable degree of freedom, preferably for measuring probes, such as strain gauges exists.

In addition, isotropic structures can be applied on the substrate, which structures can be combined with ring-shaped electrodes and thereby are independent concerning orientation.

In addition, a conceivable advantage is that from such electrode structures, large area function elements such as panel heating elements or photocells could be manufactured.

The advantages of the invention are found in particular in the substrate materials, which can be adjusted to the most varied requirements, and the adjustable structure of the conductive islands. Coated carriers for sensors can be employed for the selective detection of certain agents. The manufacturing costs for the electrical components and carrier for the sensors are low according to the invention.

BRIEF DESCRIPTION OF THE DRAWINGS

The invention is explained in more detail as an example of application based on

DETAILED DESCRIPTION OF THE PREFERRED EMBODIMENTS

Figure 1:
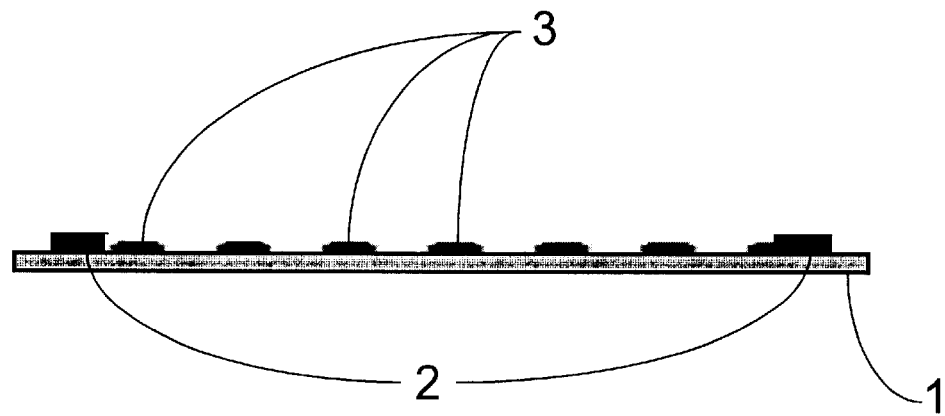
FIG. 1 as a cross section through an electrode arrangement for an electrical component and carrier for sensors and FIG. 2 as a top view of an electrode arrangement for an electrical component and carrier for sensors.
Figure 2:
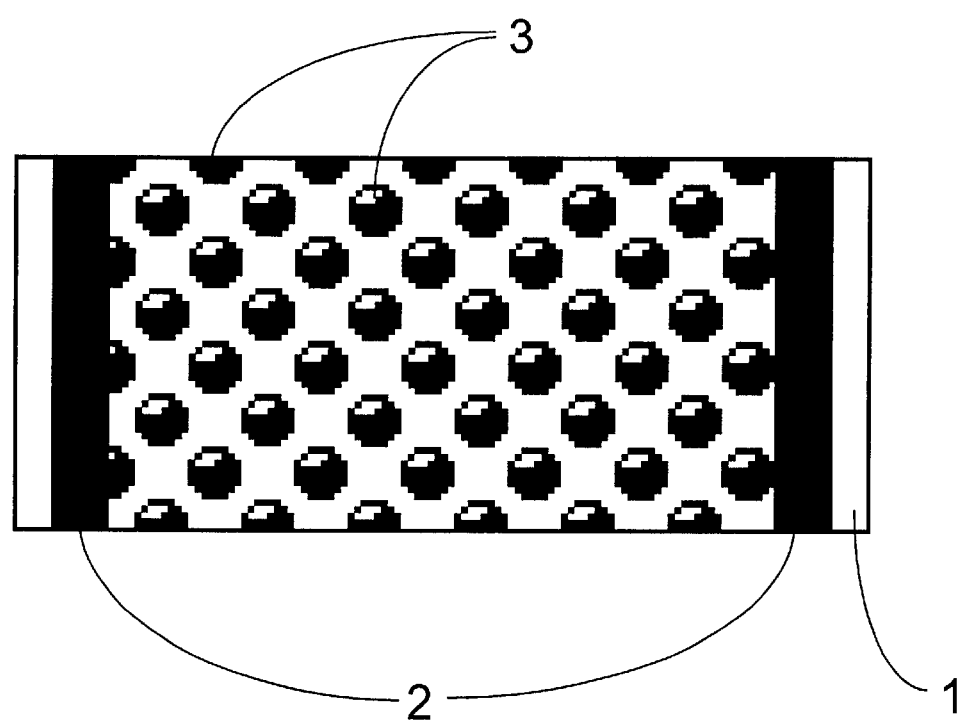

According to FIG. 1 and FIG. 2, an electrode arrangement for an electrical component and carrier for a sensor consists of a dielectric substrate (1), on which two conductive electrodes (2) for connection to normal measuring means and conductive islands (3) (=passive electrodes) are arranged. The total conductivity is determined by the partial conductivity between the conductive islands (3) over the substrate (1) and the electrodes (2). The adsorption of agents on the surface of the substrate (1) and/or on the conductive islands (3) changes the total conductance of the electrode arrangement and this conductance is evaluated as normally done and can be employed, for example, for the detection of substances.

REFERENCE SYMBOLS USED

1 Substrate
2 Electrodes
3 Conductive islands

What is claimed is:

1. An electrode arrangement for an electrical component and carrier for sensors, which arrangement is applied on a substrate (1), the arrangement consisting of two electrically conductive electrodes (2), wherein said electrodes are not electrically connected to one another, and a surface structure with suitable dimensions for representation of conductivities of the electrode arrangement and/or of a substance of a sensor-active layer by the conductance of a measuring probe or of a function element, wherein on a surface of a dielectric substrate (1) between two electrodes (2) a number of conductive islands (3), which are not or are not essentially connected with one another, are applied as a two-dimensional area arrangement.

2. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that the structure of the conductive islands (3) consists of a fine distribution of conductive substances on any insulating substrate (1).

3. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that the substance of the conductive islands (3) is firmly set on the substrate (1) and in particular it is sputtered on, steamed on, squirted on, dabbed on, imprinted or sprayed on.

4. An electrode arrangement for an electrical component and carrier for sensors, which arrangement is applied on a substrate (1), the arrangement consisting of two electrically conductive electrodes (2), wherein said electrodes are not electrically connected to one another, and a surface structure with suitable dimensions for representation of conductivities of the electrode arrangement and/or of a substance of a sensor-active layer by the conductance of a measuring probe or of a function element according to claim 1, wherein the conductive islands (3) are arranged within selected geometric figures.

5. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that the surface of the carrier for a sensor is coated with a material-selective substance.

6. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that a carrier for the sensor with a sufficiently thin substrate (1) has a sensor-active layer on all sides.

7. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that the conductive islands (3) in their short-range order show hyperstructures with anisometries of the substances with respect to the substrate.

8. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that isotropic structures of conductive islands (3) with ring-shaped electrodes (2) are arranged on the substrate (1).

9. An electrode arrangement for an electrical component and carrier for sensors, which arrangement is applied on a substrate (1), this arrangement consisting of two electrically conductive electrodes (2), which are not electrically connected with one another, and a surface structure with suitable dimensions for the representation of the conductivities of the electrode arrangement and/or of the substance of a sensor-active layer by the conductance of a measuring probe or of a function element according to claim 1, so characterized that the electrode arrangement is designed as a large area as a function element in particular as panel heating elements or photo cells.

* * * * *